(12) United States Patent
Waycuilis

(10) Patent No.: US 6,201,029 B1
(45) Date of Patent: Mar. 13, 2001

(54) STAGED COMBUSTION OF A LOW HEATING VALUE FUEL GAS FOR DRIVING A GAS TURBINE

(75) Inventor: John J. Waycuilis, Cypress, TX (US)

(73) Assignee: Marathon Oil Company, Findlay, OH (US)

( * ) Notice: Subject to any disclaimer, the term of this patent is extended or adjusted under 35 U.S.C. 154(b) by 0 days.

(21) Appl. No.: 09/150,865

(22) Filed: Sep. 10, 1998

Related U.S. Application Data (60) Continuation-in-part of application No. 08/960,297, filed on Oct. 29, 1997, which is a division of application No. 08/600,565, filed on Feb. 13, 1996, now Pat. No. 5,733,941, and a continuation-in-part of application No. 08/800,642, filed on Feb. 14, 1997, now Pat. No. 5,861,441, and a continuation-in-part of application No. 09/135,625, filed on Aug. 18, 1998, and a continuation-in-part of application No. 09/135,821, filed on Aug. 18, 1998, which is a continuation-in-part of application No. 08/600,565.

(51) Int. Cl.$^7$ .................................................. C07C 27/00
(52) U.S. Cl. ..................... 518/703; 518/704; 252/373; 60/39.2; 60/651; 431/8; 422/188
(58) Field of Search .................... 518/703, 704; 252/373; 60/39.2, 651; 431/8; 422/188

(56) References Cited

U.S. PATENT DOCUMENTS

| | | | |
|---|---|---|---|
| 2,552,308 | 8/1951 | Buchmann et al. | 260/449.6 |
| 2,660,032 | 11/1953 | Rosenthal | 60/39.02 |
| 2,686,195 | 8/1954 | McAdams | 260/449.6 |
| 3,866,411 | 2/1975 | Marion et al. | 60/39.02 |
| 3,868,817 | 3/1975 | Marion et al. | 60/39.02 |
| 3,920,579 | 11/1975 | Slater | 252/373 |
| 3,959,972 | 6/1976 | Rudolf et al. | 60/651 |
| 3,986,349 | 10/1976 | Egan | 60/39.02 |
| 4,074,981 | 2/1978 | Slater | 48/197 |
| 4,075,831 | 2/1978 | McGann | 60/39.05 |
| 4,092,825 | 6/1978 | Egan | 60/39.02 |
| 4,121,912 | 10/1978 | Barber et al. | 48/197 R |
| 4,122,670 | 10/1978 | Reider | 60/39.65 |
| 4,132,065 | 1/1979 | McGann | 60/39.02 |
| 4,158,680 | 6/1979 | McGann | 261/149 |
| 4,253,301 | 3/1981 | Vogt | 60/39.46 |
| 4,309,359 | 1/1982 | Pinto | 518/705 |
| 4,338,292 | 7/1982 | Duranleau | 423/656 |
| 4,356,698 | 11/1982 | Chamberlain | 60/733 |
| 4,399,652 | 8/1983 | Cole et al. | 60/39.465 |
| 4,434,613 | 3/1984 | Stahl et al. | 60/39.07 |
| 4,618,451 | 10/1986 | Gent | 252/373 |
| 4,678,723 | 7/1987 | Wertheim | 429/17 |
| 4,732,092 | 3/1988 | Gould | 110/229 |
| 4,833,170 | 5/1989 | Agee | 422/190 |
| 4,845,940 | 7/1989 | Beer | 60/732 |
| 4,946,477 | 8/1990 | Perka et al. | 48/197 R |
| 4,973,453 | 11/1990 | Agee | 422/190 |
| 5,026,934 | 6/1991 | Bains et al. | 588/314 |
| 5,177,114 | 1/1993 | Van Dijk et al. | 518/703 |
| 5,245,110 | 9/1993 | Van Dijk et al. | 585/946 |
| 5,295,356 | 3/1994 | Billy | 62/20 |
| 5,318,436 | 6/1994 | Colket, III et al. | 431/8 |
| 5,319,935 | 6/1994 | Toon et al. | 60/733 |
| 5,472,986 | 12/1995 | Van Dijk | 518/705 |

FOREIGN PATENT DOCUMENTS 0 497 425 A1  8/1992  (EP).
4-364142  12/1992  (JP).

OTHER PUBLICATIONS

Hedden, K., et al., "A New Concept for the Production of Liquid Hydrocarbons from Natural Gas in Remote Areas", Oil Gas—European Magazine, Mar. 1994, pp. 42–44.

"The Syntroleum Process" promotional flier, Aug., 1994.

*Primary Examiner*—Johann Richter
*Assistant Examiner*—Sreeni Padmanabhan
(74) *Attorney, Agent, or Firm*—Jack E. Ebel (57) ABSTRACT

A process is provided for combusting a low heating value fuel gas in a combustor to drive an associated gas turbine. A low heating value fuel gas feed is divided into a burner portion and a combustion chamber portion. The combustion chamber portion and a combustion air are conveyed into a mixing zone of the combustor to form an air/fuel mixture. The burner portion is conveyed into a flame zone of the combustor through a burner nozzle while a first portion of the air/fuel mixture is conveyed into the flame zone through a burner port adjacent to the burner nozzle. The burner portion and first portion of the air/fuel mixture are contacted in the flame zone to combust the portions and produce flame zone products. The flame zone products are conveyed into an oxidation zone of the combustor downstream of the flame zone while a second portion of the air/fuel mixture is also conveyed into the oxidation zone. The second portion is combusted in the oxidation zone in the presence of the flame zone products to produce combustion products. The combustion products are conveyed into the associated gas turbine and drive the gas turbine.

23 Claims, 5 Drawing Sheets

STAGED COMBUSTION OF A LOW HEATING VALUE FUEL GAS FOR DRIVING A GAS TURBINE

CROSS REFERENCES

This is a continuation in part of my U.S. patent application Ser. No. 08/960,297 filed on Oct. 29, 1997, which is a divisional of U.S. Ser. No. 08/600,565, filed Feb. 13, 1996, now U.S. Pat. No. 5,733.941 issued on Mar. 31, 1998. This is also a continuation in part of my U.S. patent applications Ser. No. 08/800,642 now U.S. Pat. No. 5,861,441 and U.S. Ser. Nos. 09/135,625; and 09/135,821 filed on Feb. 14, 1997, Aug. 18, 1998, and Aug. 18, 1998, respectively, which are continuations in part of U.S. Ser. No. 08/600,565 filed on Feb. 13, 1996 now U.S. Pat. No. 5,733,941.

BACKGROUND OF THE INVENTION

1. Technical Field

The present invention relates generally to a process for combusting a fuel gas to drive a gas turbine and, more particularly, to a process for combusting a low heating value fuel gas in a combustor by dividing the fuel gas into a plurality of portions and combusting each portion of the fuel gas in a different stage of the combustor.

2. Background Information

Standard commercial combustors for gas turbines employ burner assemblies and combustion chambers typically designed to combust relatively high heating value fuels, such as natural gas which has a heating value in a range from about 50,000 to 60,000 kJ/kg. The stoichiometric demand for air in a conventional commercial burner assembly combusting a high heating value fuel gas is usually at least 10 volumes of combustion air for each volume of fuel gas fed to the burner assembly. In accordance with the swirl-stabilized combustion mechanism utilized by most commercial burner assemblies, the combustion air is fed to the combustion chamber through an annular flow region of the burner assembly which encircles a central burner nozzle. Fixed vanes are positioned in the annular flow region which impart a spin to the combustion air feed creating an air vortex. The burner fuel gas is fed into the interior zone or "eye" of the air vortex via the burner nozzle. The velocities of the feed streams are relatively low at the interface of the fuel-rich edge and the air-rich "eye wall" of the vortex which enables a stable film of laminar diffusion combustion to occur at the interface.

In contrast, the stoichiometric demand for air when combusting a low heating value fuel gas in a burner assembly is substantially less than when combusting a high heating value fuel gas. Low heating value fuel gases contain significant quantities of inert components termed "ballast" gases, such as nitrogen, carbon dioxide, water vapor and the like, which are not combustible and which dilute the remaining combustible components of the fuel gas. Accordingly, the stoichiometric ratio of air to fuel gas in a burner assembly receiving a low heating value fuel gas is generally much less than 10:1 on a volumetric basis, and may be even less than 1:1 for certain fuel gases. As such, a conventional central burner nozzle, which is designed for high heating value fuel gases, is not sufficiently large to accommodate the large volume of low heating value fuel gas required to achieve the necessary heat release for the burner assembly. Conversely, the annular flow region is overly large, permitting an excessive air to fuel ratio in the burner assembly which is outside the flammability envelope of the air/fuel mixture.

Specialized combustors for combusting low heating value fuel gases have been developed at high cost for specific applications, such as for combusting blast furnace gases produced in the manufacture of steel. For example, Asai Brown Boveri Corp. has designed a gas turbine, Model No. 11N-2, which utilizes an oversized burner assembly to accommodate the mass flow of the low heating value fuel gas and utilizes undersized air "swirlers" to ensure a correct ratio of air to fuel in the burner assembly. However, this design is only operable within a narrow range of conditions and cannot be utilized with turbines having internal combustors. Thus, it is apparent that a need exists for an effective process which combusts a low heating value fuel gas and utilizes the resulting gaseous combustion products to drive a gas turbine.

Accordingly, it is an object of the present invention to provide an effective process for combusting a low heating value fuel gas in a combustor associated with a gas turbine and driving the gas turbine with the resulting gaseous combustion products. More particularly, it is an object of the present invention to provide substantially complete combustion of the low heating value fuel gas by dividing the low heating value fuel gas and combusting the divided portions of the low heating value fuel gas in different stages of a combustor. It is another object of the present invention to provide such a combustion process utilizing conventional combustors which are retrofitted at low cost to accommodate the low heating value fuel gas. It is yet another object of the present invention to provide such a combustion process which emits substantially reduced levels of contaminants to the environment. These objects and others are achieved in accordance with the invention described hereafter.

SUMMARY OF THE INVENTION

The present invention is a process for combusting a low heating value fuel gas in a combustor to drive an associated gas turbine. A combustor having utility in the present process comprises a burner nozzle, a combustor casing, and a combustion liner. The burner nozzle and combustion liner are mounted within the combustor casing, with the combustion liner being positioned downstream of the burner nozzle. The combustor casing and combustion liner define an annulus between them, including a mixing zone which is upstream of the burner nozzle and combustion liner. The combustion liner encloses a combustion chamber which includes a flame zone proximal to the burner nozzle and an oxidation zone downstream of the flame zone. A plurality of injectors are provided in the combustor casing upstream of the burner nozzle. A plurality of combustion chamber ports are provided in the combustion liner downstream of the injectors and burner nozzle.

The process comprises dividing a low heating value fuel gas feed into a relatively small minority burner portion and a relatively large majority combustion chamber portion. The combustion chamber portion of the low heating value gas feed is conveyed into the mixing zone through the injectors in the combustor casing. A combustion air is also conveyed through the annulus into the mixing zone and mixed with the low heating value gas feed at a relatively high velocity to form an air/fuel mixture. The ratio of combustible components to air in the resulting air/fuel mixture is substoichiometric and below the normal flammability limit.

A first portion of the air/fuel mixture is conveyed into the flame zone through a burner port which is adjacent to, but fluid isolated from the burner nozzle. A burner fuel gas, which includes the burner portion of the low heating value gas feed, is simultaneously conveyed into the flame zone through the burner nozzle. The burner fuel gas may also include a high heating value fuel gas feed to increase the overall heating value of the burner fuel gas. In any case, the burner fuel gas and first portion of the air/fuel mixture enter the flame zone in relative amounts such that the ratio of combustible components to air in the flame zone approximates a stoichiometric ratio which is within the normal flammability limit and supports a diffusion combustion flame.

The burner fuel gas contacts the first portion of the air/fuel mixture in the flame zone at a relatively low velocity, creating a diffusion combustion flame which combusts the combustible components present in the flame zone and produces flame zone products. The resulting flame zone products are conveyed from the flame zone into the oxidation zone. A second portion of the air/fuel mixture is also conveyed into the oxidation zone from the mixing zone through the combustion chamber ports. The second portion of the air/fuel mixture is combusted in the oxidation zone in the presence of the flame zone products to produce combustion products. The combustion products are conveyed into a gas turbine and drive the gas turbine.

In accordance with a specific embodiment of the present invention, the first portion of the air/fuel mixture is conveyed from the mixing zone to the burner port countercurrent to the direction of flow in the combustion chamber. Similarly, the second portion of the air/fuel mixture is conveyed from the mixing zone to the combustion chamber ports countercurrent to the direction of flow in the combustion chamber. The combustion air is also conveyed into the mixing zone countercurrent to the direction of flow in the combustion chamber.

In accordance with another a specific embodiment of the present invention, the above-described combustion process is adapted for integration into a process for converting a hydrocarbon gas to a synthetic hydrocarbon liquid. The process comprises reacting a first portion of an air feed and a lighter hydrocarbon feed gas to produce a synthesis gas including hydrogen and carbon monoxide. The synthesis gas is reacted in the presence of a hydrocarbon synthesis catalyst to produce heavier hydrocarbons, a tail gas and water. The tail gas is a low heating value fuel gas containing at least about 80 mole percent inert non-combustible components. The low heating value tail gas is separated from the other products and combusted in a combustor with a second portion of the air feed in substantially the same manner as described above. Mechanical power is generated from the resulting combustion products and the mechanical power is used to compress the air feed.

The invention will be further understood from the accompanying drawings and description.

DESCRIPTION OF PREFERRED EMBODIMENTS

Figure 1:
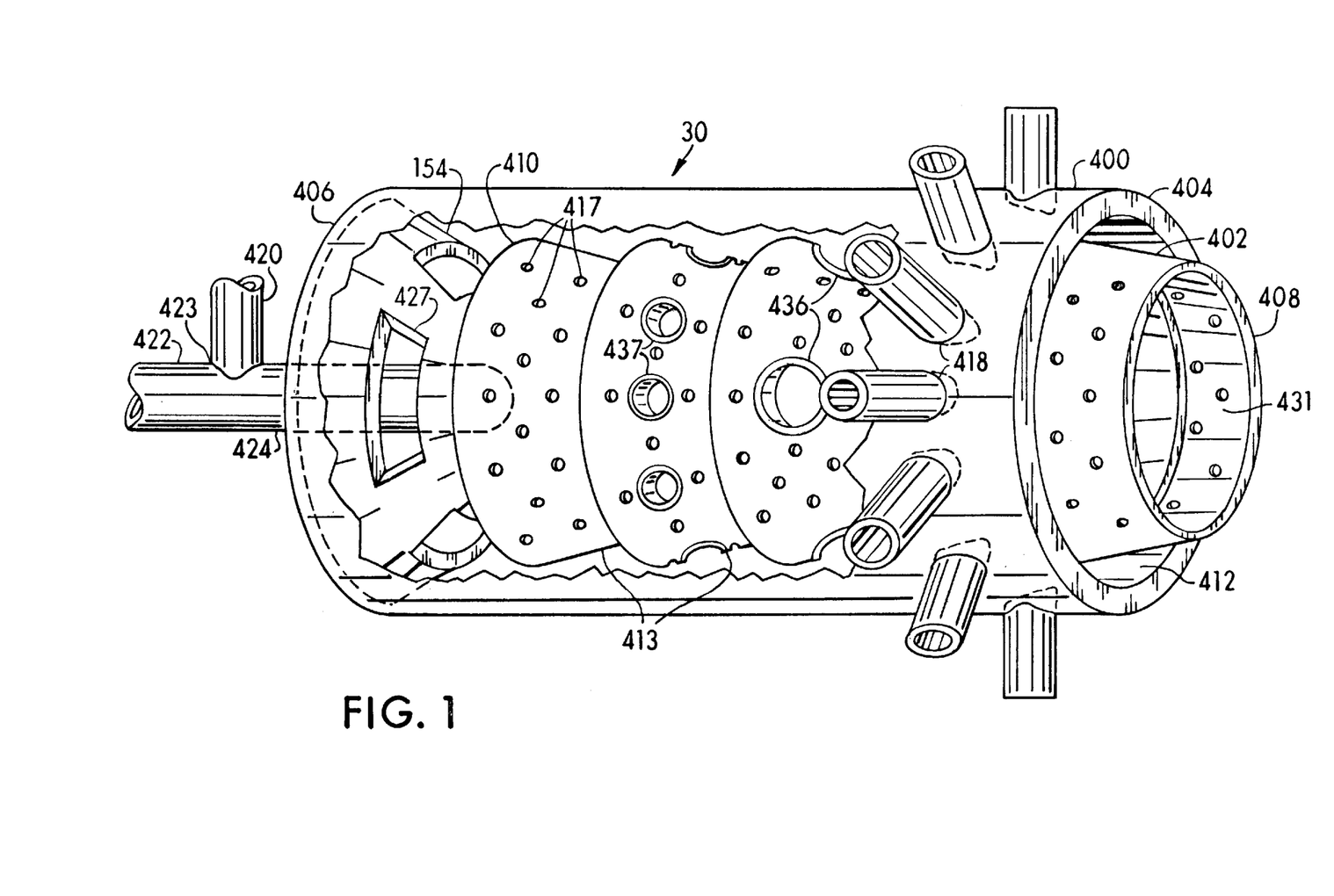
FIG. 1 is a perspective view of a combustor having utility in a combustion process of the present invention.

The present invention relates to a process for combusting a low heating value (LHV) fuel gas in a combustor and driving an associated gas turbine with the resulting hot gaseous combustion products. Referring initially to FIG. 1, a combustor, generally designated 30, is shown which has utility in the combustion process of the present invention. The combustor 30 is termed an "external combustor" because it is not structurally integral with the associated gas turbine (not shown in FIG. 1). It is noted, however, that practice of the present process is not limited to external combustors. As will be apparent to the skilled artisan, the present process may likewise be practiced with internal combustors which are structurally integral with the associated gas turbine.

The combustor 30 described herein for purposes of illustration includes a casing 400, termed the "combustor can", and a combustion liner 402. The combustor can 400 is cylindrically configured with a substantially open upstream end 404 and a dome-shaped, substantially closed downstream end 406. Conversely, the combustion liner 402 is cylindrically configured with a substantially open downstream end 408 and a dome-shaped, substantially closed upstream end 410. The combustion liner 402 is concentrically positioned within the combustor can 400 and has a substantially smaller diameter than the combustor can 400 to define a mixing annulus 412 between the combustor can 400 and the combustion liner 402 which opens into the upstream end 404 of the combustor can 400. As related to the combustor 30, the terms "downstream" and "upstream" are used herein with reference to the flow direction of the gaseous flame zone and combustion products within the combustor 30.

Figure 2:
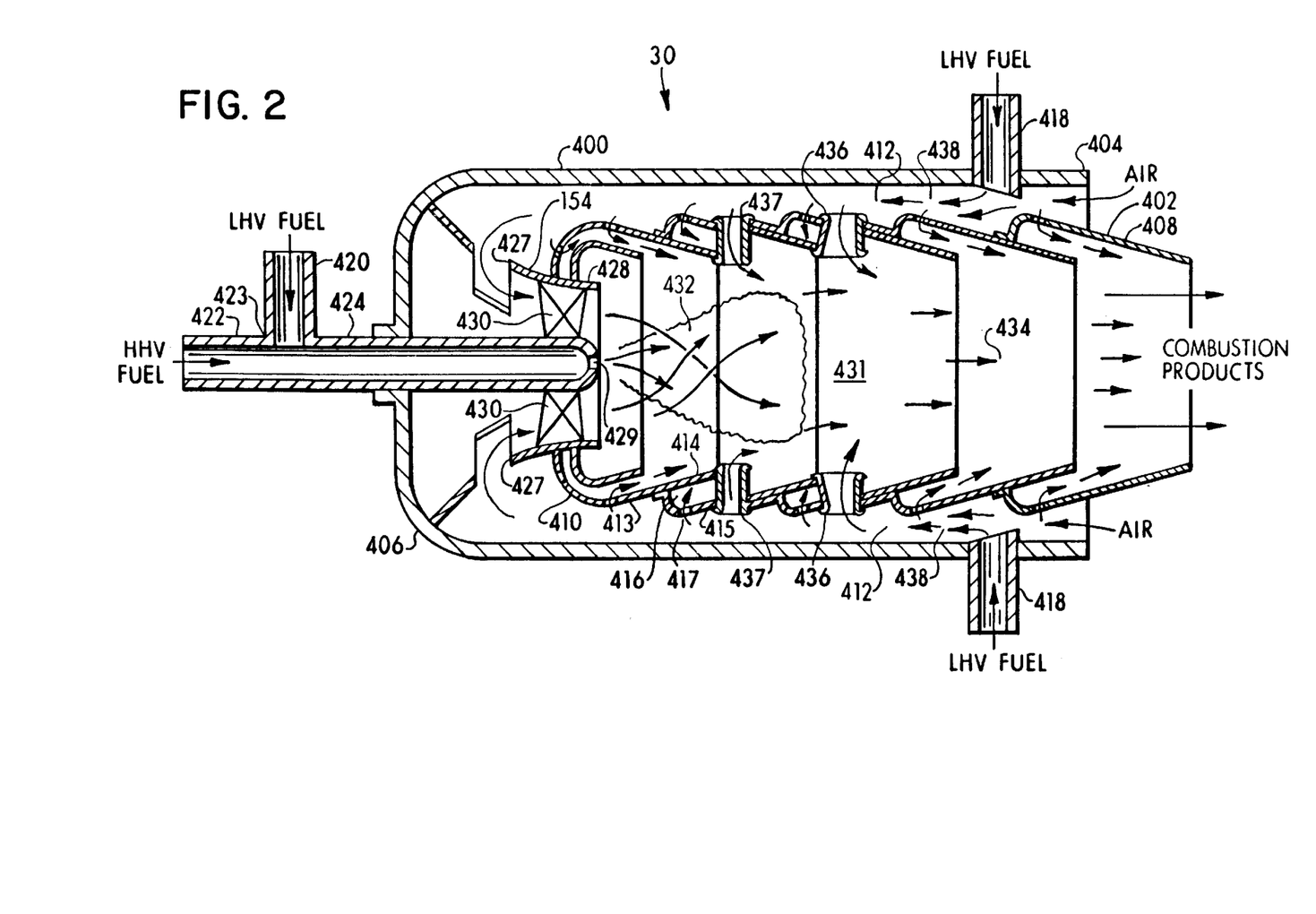
FIG. 2 is a cross-sectional view of the combustor shown in FIG. 1.

Referring additionally to FIG. 2, the combustion liner 402 is constructed from a plurality of sequentially overlapping segments 413. The downstream end 414 of each segment 413 is nested within the upstream end 415 of the succeeding segment 413 to form a sequence of annular cooling spaces 416 around the circumference of the combustion liner 402. A plurality of cooling perforations 417 are also provided in substantially the entire outer surface of the combustion liner 402.

A plurality of LHV fuel gas injectors 418, typically numbering from 4 to 12, are radially disposed around the circumference of the combustor can 400 proximal to the upstream end 404 of the combustor can 400. The LHV fuel gas injectors 418 may broadly encompass any type of opening through the combustor can 400 or any injection device directed through the combustor can 400. An LHV fuel gas burner line 420 and a high heating value (HHV) fuel gas burner line 422 are positioned external to the combustor can 400 and join at a junction point 423 to form a burner feed line 424 carrying a burner fuel gas which passes through the downstream end 406 of the combustor can 400.

The combustor 30 further includes a burner assembly 154 positioned at the upstream end 410 of the combustion liner 402. The burner assembly 154 has a plurality of external burner ports 427 in fluid communication with the mixing annulus 412. The burner assembly 154 also has a central burner port 428 and a central burner nozzle 429, which concentrically penetrates the central burner port 428. Fixed swirling vanes 430 are positioned in the central burner port 428 surrounding the central burner nozzle 429. The central burner port 428 and central burner nozzle 429 discharge into the open interior of the combustion liner 402 which defines a combustion chamber 431. The central burner port 428 and central burner nozzle 429 are in fluid isolation with respect to one another such that fluids in the central burner nozzle 429 do not substantially commingle with fluids in the central burner port 428 until the fluids have exited the central burner nozzle 429 and central burner port 428, respectively, into the combustion chamber 431.

The combustion chamber 431 comprises a plurality of stages or zones including a flame zone 432 proximal to the upstream end 410 of the combustion liner 402 at the discharge of the central burner port 428 and central burner nozzle 429 and an oxidation zone 434 downstream of the flame zone 432 proximal to the downstream end 408 of the combustion liner 402. A plurality of primary combustion chamber ports 436 and secondary combustion chamber ports 437 are radially disposed around the circumference of the combustion liner 402 downstream of the LHV fuel gas injectors 418. The primary and secondary combustion chamber ports 436, 437 enter the combustion chamber 431 approximately between the flame zone 432 and the oxidation zone 434, providing fluid communication between the mixing annulus 412 and the combustion chamber 431. The region of the mixing annulus 412 positioned between the LHV fuel gas injectors 418 and the primary combustion chamber ports 436 is termed the high velocity mixing zone 438.

The combustor 30 is preferably fabricated from a conventional external can combustor. In particular, the combustor 30 is preferably fabricated by retrofitting a conventional external can combustor with an LHV fuel gas burner line 420, LHV fuel gas injectors 418, and any additional elements taught herein, as required. Combustors having utility in the present combustion process may likewise be fabricated by retrofitting one of the various types of conventional internal combustors in a similar manner, as is apparent to the skilled artisan. Thus, conventional equipment is readily adapted at a relatively low cost enabling practice of the present combustion process. The resulting combustor is a high temperature vessel typically operable within a sustained temperature range of about 1000 to 2000° C., and a sustained pressure range of about 800 to 1,100 kPa.

Figure 3:
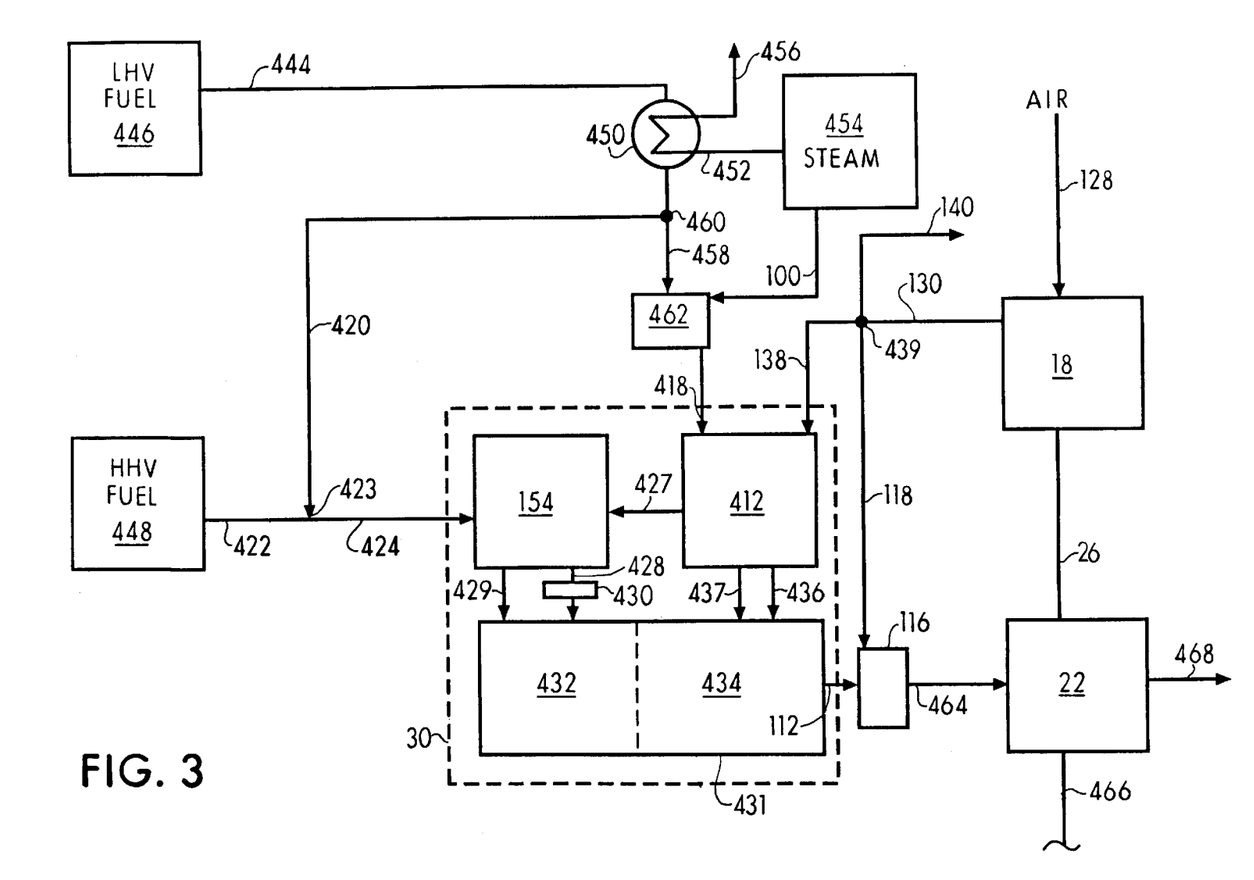
FIG. 3 is a schematic of a combustion process of the present invention.

Practice of the combustion process is described with further reference to FIG. 3. The combustion process is practiced in a continuous steady-state manner by conveying an LHV fuel gas feed through an LHV fuel gas feed line 444 from an LHV fuel gas source 446, while conveying an HHV fuel gas feed through the HHV fuel gas burner line 422 from an HHV fuel gas source 448, as needed. The HHV fuel gas has a relatively high heating value in a range of about 50,000 to 60,000 kJ/kg, which is characteristic of natural gas. The LHV fuel gas has a relatively low heating value in a range of about 1,500 to 3,000 kJ/kg, which is characteristic of waste gases or otherwise unusable gases containing only dilute quantities of combustible components. LHV fuel gases having utility herein include subquality gas containing substantial quantities of nitrogen and/or carbon dioxide or gas derived from a coal seam, landfill or sewage treatment plant. A specific LHV fuel gas having utility herein is a tail gas from a hydrocarbon gas to liquid conversion process, wherein the tail gas comprises nitrogen, carbon dioxide, carbon monoxide, hydrogen, water and light hydrocarbons typically having a molar composition range of about 75 to 90% $N_2$, 4 to 5% $CO_2$, 2 to 7% CO, 1 to 10% $H_2$, 0.1 to 0.5% $H_2O$ and the remainder hydrocarbons. The tail gas contains inert non-combustible components in a range of about 80 to 94 mole %, and preferably containing at least about 90 mole % inert non-combustible components, with the remainder being oxygen and combustible components. Inert non-combustible components are defined herein as components which will not react exothermically with oxygen. Such components include nitrogen, argon, carbon dioxide and water. Combustible components are defined herein as components which may react exothermically with oxygen at elevated temperatures. Such components include carbon monoxide, hydrogen, alcohols, methane and heavier hydrocarbons.

A preheater 450 is positioned in the LHV fuel gas feed line 444. The LHV fuel gas is preheated in the preheater 450 by steam entering the preheater 450 through a steam inlet line 452 from a steam source 454 at a temperature in a range of about 300 to 400° C., and exiting the preheater 450 as a steam and/or a condensate through a steam/condensate outlet line 456 at a temperature in a range of about 100 to 250° C. The preheated LHV fuel gas exits the preheater 450 at a temperature in a range of about 150 to 350° C. and a pressure in a range of about 1,000 to 2,000 kPa. Preheating the LHV fuel gas, in conjunction with the hot high-pressure air feed, widens the flammability envelope and stabilizes combustion in the combustion chamber 431 as will be described hereafter.

The LHV fuel gas feed line 444 splits into the LHV fuel gas burner line 420 and an LHV fuel gas combustion chamber line 458 at a junction point 460 after the preheater 450. The preheated LHV fuel gas feed is correspondingly divided into a burner portion and a combustion chamber portion, with the combustion chamber portion passing through the LHV fuel gas combustion chamber line 458 and the burner portion passing through the LHV fuel gas burner line 420. The volumetric ratio of the combustion chamber portion to the burner portion of the LHV fuel gas is in a range of about 9:1 to 3:1. The HHV fuel gas burner line 422 and LHV fuel gas burner line 420 join in the burner feed line 424 at the junction point 423, wherein the burner portion of the LHV fuel gas feed mixes with the HHV fuel gas feed (if any is present) to form a burner fuel gas which is conveyed into the burner assembly 154 via the burner feed line 424. The burner fuel gas is typically fed to the burner assembly 154 at a rate of about 1,000 to 1,500 m³/hr, a temperature in a range of about 5 to 300° C. and a pressure in a range of about 1,000 to 2,000 kPa. The volumetric ratio of HHV fuel gas to LHV fuel gas in the burner fuel gas is in a range of about 1:10 to 1:3. The burner fuel gas has a resulting heating value in a range of about 5,000 to 10,000 kJ/kg.

The combustion chamber portion of the LHV fuel gas is conveyed via the LHV fuel gas combustion chamber line 458 to an LHV fuel gas header 462 at a rate of about 3,000 to 5,000 m³/hr, a temperature in a range of about 150 to 350° C., and a pressure in a range of about 1,000 to 2,000 kPa. The LHV fuel gas header 462 distributes the combustion chamber portion of the LHV fuel gas to the LHV fuel gas injectors 418. The LHV fuel gas injectors 418 direct the LHV fuel gas at a high velocity downstream into the high velocity mixing zone 438 of the mixing annulus 412.

An air feed is drawn through an air feed inlet line 128 into an air compressor 18 at a rate in a range of about 25,000 to 35,000 kg/hr, a temperature of about 15° C. or ambient, and a pressure at about atmospheric. The air compressor 18 compresses the air feed to a pressure in a range of about 800 to 1,100 kPa and a temperature in a range of about 325 to 375° C. The resulting compressed air feed is conveyed via an air compressor outlet 130 to a junction point 439 at a rate in a range of about 25,000 to 35,000 kg/hr. The compressed air feed is divided into a combustion air, a bleed air and a cooling air at the junction point 439, with the volumetric ratio of cooling air to combustion air to bleed air in a range of about 2:90:8 to 2:28:70. The bleed air is vented via an air bleed line 140 or recovered for another use (not shown). The combustion air is conveyed into the mixing annulus 412 via a combustion air inlet line 138. The combustion air travels downstream at a high velocity through the mixing annulus 412 into the high velocity mixing zone 438 where the combustion air mixes at a high velocity on the order of about 10 to 30 m/sec with the combustion zone portion of the LHV fuel gas to form an air/fuel mixture. The volumetric ratio of air to fuel in the mixture is in a range of about 4:1 to 1:1. From about 75 to 85% by volume of the air/fuel mixture is diverted from the mixing annulus 412 into the combustion chamber 431 via the primary and secondary combustion chamber ports 436, 437. The remainder of the air/fuel mixture continues traveling downstream through the mixing annulus 112 to the burner assembly 154 where the remainder of the air/fuel mixture is diverted into the combustion chamber 431 via the external burner ports 427 and the central burner port 428. Steam at a pressure in a range of about 1,000 to 1,500 kPa and a temperature in a range of about 350 to 465° C. may optionally be fed to the combustion chamber 431 from the steam source 454 via a combustor steam feed line 100, the LHV fuel gas header 462 and the LHV fuel gas injectors 418 at a feed rate in a range of about 0 to 8,000 kg/hr.

The swirling vanes 430 positioned in the central burner port 428 impart a spin to the air/fuel mixture as it enters the combustion chamber 431 creating an air/fuel mixture vortex within the combustion chamber 431 proximal to the central burner nozzle 429. The burner fuel gas is simultaneously fed through the burner assembly 154 and discharged from the central burner nozzle 429 into the eye of the vortex. The velocities of the burner fuel gas and air/fuel mixture are on the order of about 0.4 m/sec or less at their interface which is slow relative to the velocities of the combustion air and LHV fuel gas in the high velocity mixing zone 438. The slow velocity interface of the burner fuel gas and air/fuel mixture produces a stable diffusion flame within the flame zone 432 of the combustion chamber 431 which exhibits a desirable near-stoichiometric ratio of air to fuel gas and oxidizes the combustible components contained in the burner fuel gas. The average temperature of the flame zone 432 is in a range of about 1100 to about 1600° C., which is relatively low and substantially inhibits the formation of undesirable oxides of nitrogen in the combustor 30.

The product of the flame zone 432 is conveyed downstream to the oxidation zone 434 along with the air/fuel mixture entering the combustion chamber 431 via the primary and secondary combustion chamber ports 436, 437. Substantially all of the combustible components present in the oxidation zone 434 are oxidized therein with or without flame formation to yield hot gaseous combustion products. The average temperature of the oxidation zone 434 is in a range of about 900 to about 1100° C., which is likewise relatively low to substantially inhibit the formation of undesirable oxides of nitrogen in the combustor 30. The relatively low temperature also desirably reduces radiation and other heating effects in the combustor 30, the reduction of which tends to increase the operating life of the combustor components. Nevertheless, the resulting heat release efficiency of combustion of the LHV fuel gas in the combustion chamber 431 is at a satisfactory level in a range of about 99.5 to near 100%. The combustion products are discharged from the combustor 30 via the downstream end 410 of the combustion liner 402 at a rate of about 17,000 to 28,000 m$^3$/hr, a temperature in a range of about 850 to 1150° C., and a pressure in a range of about 800 to 1,000 kPa. The combustion products typically have a molar composition range of about 65 to 80% $N_2$, 1 to 14% $O_2$, 3 to 8% $CO_2$, 3 to 13% $H_2O$, <1% $H_2$, <0.02% CO, <0.01% oxides of nitrogen, and <0.01% hydrocarbons.

It is noted that a very small portion of the combustion air and air/fuel mixture also serves a cooling function to protect the combustion liner 402 from excess heating. In particular, the combustion air and air/fuel mixture cool the combustion liner 402 by flowing from the mixing annulus 112 through the perforations 417 and annular cooling spaces 416 to form a cooling film adjacent to the combustion liner 402 which cools the combustion liner 402 and subsequently exits the combustor 30 with the combustion products.

The combustion products are conveyed to a gas manifold 116 via a combustor outlet line 112 where the combustion products are mixed with the cooling air conveyed to the gas manifold 116 via a cooling air line 118. The volumetric ratio of cooling air to combustion products is in a range of about 1:100 to 3:100. The mixture of combustion products and cooling air is fed to a gas turbine 22 via a gas turbine line 464 at a rate of about 17,170 to 28,840 m$^3$/hr, a temperature in a range of about 850 to 1150° C., and a pressure in a range of about 800 to 1,100 kPa, thereby driving the blades and discs of the gas turbine 22. The gas turbine 22 functions as a power turbine, being mechanically linked by a first shaft 26 to the air compressor 18, thereby driving the air compressor 18. The gas turbine 22 is also be provided with a second shaft 466 in accordance with one embodiment, which is linked to an electrical generator (not shown) generating electrical power for export. In accordance with an alternate embodiment, mechanical power is derived from the second shaft 466 for export. The mixture of combustion products and cooling air exits the gas turbine 22 at a temperature in a range of about 450 to 750° C. and a pressure in a range of about 100 to 300 kPa via a turbine outlet line 468 and is conveyed to a secondary power turbine (not shown) or discharged to the atmosphere via a flue (not shown).

The present combustion process has been described above during steady-state operation. Start-up operation of the combustion process is effectuated by initially feeding only the HHV fuel gas as a pilot gas to the burner assembly 154 via the HHV fuel gas burner line 422 and burner feed line 424 in the absence of the LHV fuel gas. The burner assembly 154 may be provided with an ignitor (not shown) to initiate a diffusion flame. Once the stable diffusion flame is established in the flame zone 432, the LHV fuel gas feed to the burner assembly 154 is initiated in a relatively small amount via the LHV burner gas line 420 and burner feed line 424. The ratio of LHV fuel gas to HHV fuel gas in the burner gas is gradually increased thereafter until the desired ratio for steady-state operation of the combustor 30 is achieved.

The present combustion process has a number of alternate embodiments within the scope of the present invention. In accordance with one alternate embodiment, the volumetric ratio of HHV fuel gas to LHV fuel gas in the burner fuel gas may range from 1:10 to 1:∞ such that the resulting burner fuel gas is exclusively LHV fuel gas, with substantially no HHV fuel gas being fed to the central burner nozzle 429. Alternatively, the volumetric ratio of HHV fuel gas to LHV fuel gas in the burner fuel gas may range from 1:3 to 1:0 such that the resulting burner fuel gas is exclusively HHV fuel gas, with substantially no LHV fuel gas being fed to the central burner nozzle 429. The present combustion process has also been described above as operable in a countercurrent manner, wherein the air/fuel mixture is conveyed from the high velocity mixing zone 438 to the ports 427, 436, 437 countercurrent to the direction of gas flow in the combustion chamber 431. Similarly, the combustion air is conveyed into the high velocity mixing zone 438 countercurrent to the direction of gas flow in the combustion chamber 431. It is apparent to the skilled artisan that, within the scope of the present invention, the combustion process is operable in a cocurrent manner, wherein the combustor 30 is reconfigured, enabling the air/fuel mixture to be conveyed from a high velocity mixing zone to combustion ports cocurrent to the direction of gas flow in the combustion chamber and/or similarly enabling the combustion air to be conveyed into a high velocity mixing zone cocurrent to the direction of gas flow in the combustion chamber.

Figure 4:
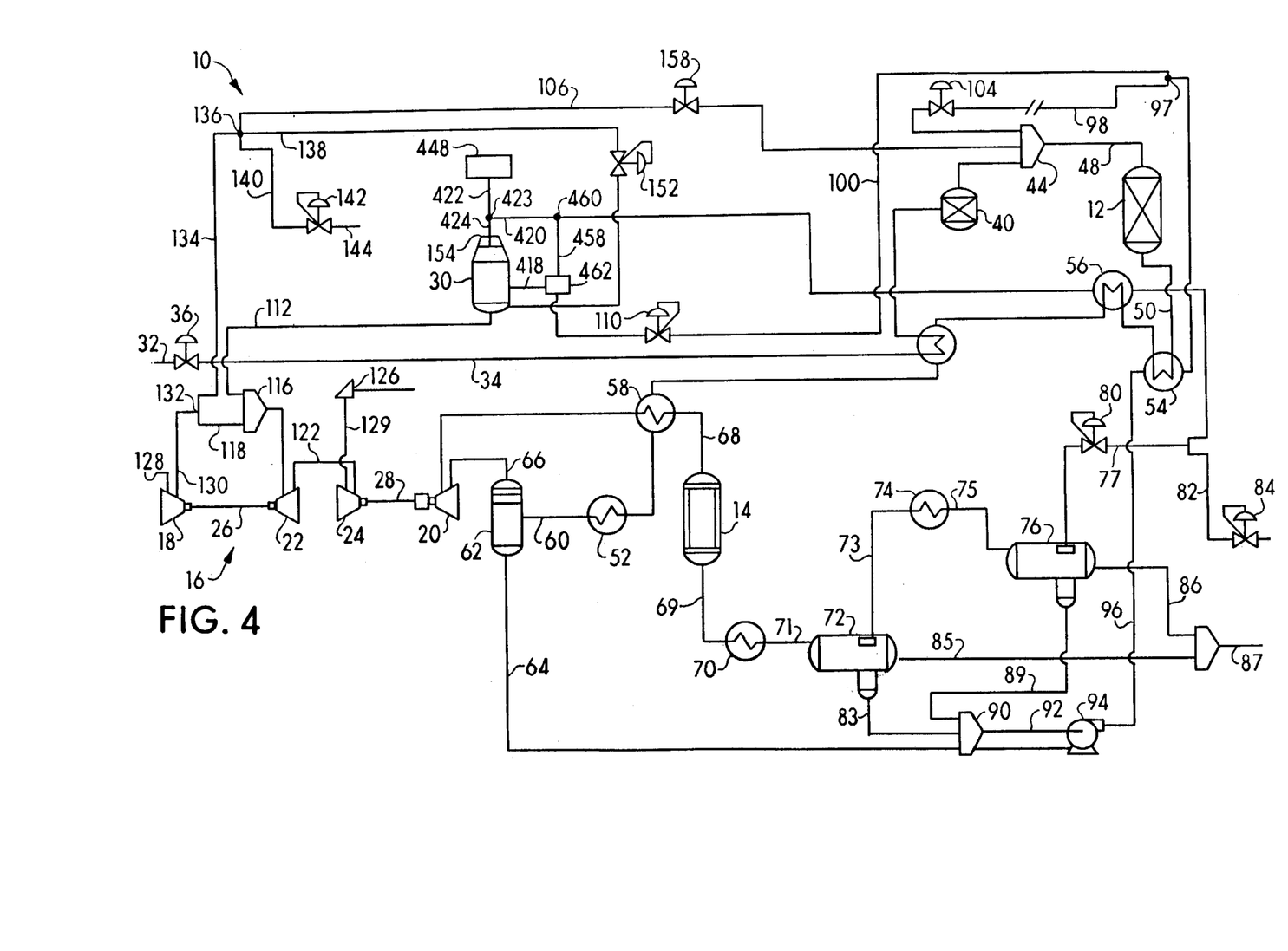
FIG. 4 is a schematic of the combustion process of the present invention adapted for integration into a process for converting a hydrocarbon gas to a synthetic hydrocarbon liquid.

In yet another alternate embodiment of the present invention, the above-described combustion process may be adapted for integration into a process for converting a hydrocarbon gas to a synthetic hydrocarbon liquid, such as described in U.S. Pat. No. 5,733,941, incorporated herein by reference. Referring to FIG. 4, a system of interconnected process equipment for practicing a hydrocarbon conversion process including the combustion process of the present invention is generally designated 10. The components of the system 10 shown in FIG. 4 which are common to FIGS. 1–4 are designated by common reference characters.

The system 10 comprises three primary operational units. The first unit is an autothermal reformer (ATR) 12 which is provided to reform a hydrocarbon feed gas, compressed air and steam into a synthesis gas. The second unit is a Fischer-Tropsch reactor (F/T reactor) 14 which is provided to convert the synthesis gas to a synthetic hydrocarbon liquid. The third unit is a Brayton cycle 16 which is provided to compress the air feed to the ATR 12 utilizing power generated by combustion of an LHV fuel gas in substantially the same manner as described above, wherein the LHV fuel gas is the F/T reactor tail gas. The Brayton cycle 16 includes the first air compressor/gas turbine pair 18, 22 mechanically linked by the first shaft 26, a second synthesis gas compressor/gas turbine pair 20, 24 mechanically linked by another shaft 28, and the combustor 30 which produces the hot gaseous combustion products for driving the first and second gas turbines 22, 24.

More particularly, the system 10 comprises a hydrocarbon feed gas inlet 32 through which a hydrocarbon feed gas is supplied to the system 10. The hydrocarbon feed gas is typically fed through the hydrocarbon feed gas inlet 32 at a rate of about 8,000 to 12,000 m$^3$/hr, a temperature in a range of about 16 to 67° C., and a pressure in a range of about 1,000 to 10,000 kPa. The hydrocarbon feed gas is preferably a naturally-occurring, non-synthetic hydrocarbon gas produced from a subsurface formation. Among such gases, natural gas is most preferred, although other hydrocarbon feed gases have utility herein, including subquality gas containing nitrogen and/or carbon dioxide, gas derived from coal seams or gas derived from ocean hydrates. A hydrocarbon feed gas inlet line 34, having a hydrocarbon feed gas pressure control valve 36 positioned therein, connects to the hydrocarbon feed gas inlet 32 and conveys the hydrocarbon feed gas downstream in the direction of the ATR 12. Also serially positioned in the hydrocarbon feed gas inlet line 34 downstream of the hydrocarbon feed gas inlet 32 are a hydrocarbon feed gas heat exchanger 38 and an H$_2$S removal unit 40. The hydrocarbon feed gas heat exchanger 38 preheats the hydrocarbon feed gas to a temperature in a range of about 380 to 450° C. by means of a high-temperature synthesis gas exiting the ATR 12, as described hereafter. The preheated hydrocarbon feed gas has a resultant pressure in a range of about 900 to 1,100 kPa. The H$_2$S removal unit 40 is a zinc oxide bed which substantially removes all H$_2$S present in the preheated hydrocarbon feed gas via chemical reaction with the zinc oxide.

The hydrocarbon feed gas line 34 extends from the hydrocarbon feed gas inlet 32 to an ATR carburetor 44. Air and stream also feed into the ATR carburetor 44 from an air and steam source described hereafter. The ATR carburetor 44 mixes the hydrocarbon feed gas from the hydrocarbon feed gas line 34 with the air and steam and an ATR inlet gas mixture line 48 exits the ATR carburetor 44 carrying the gaseous mixture comprising the hydrocarbon feed gas, air and steam (termed the ATR inlet gas mixture) from the ATR carburetor 44 to the ATR 12. The composition of the ATR inlet gas mixture is selected in accordance with the requirements of the ATR 12 and the desired composition of the final synthetic hydrocarbon liquid product. The ATR inlet gas mixture typically has a molar composition in a range of about 3.0 to 3.5 moles of air and about 0.15 to 0.30 moles of steam per mole of hydrocarbon feed gas and is supplied to the ATR 12 at a combined rate of about 35,000 to 50,000 m$^3$/hr, a temperature in a range of about 350 to 450° C., and a pressure in a range of about 900 to 1,100 kPa.

The ATR 12 is a high-temperature reactor vessel, wherein the ATR inlet gas mixture is adiabatically reacted to produce a synthesis gas containing H$_2$ and CO, preferably in a molar ratio of about 2:1, although other ratios are possible within the scope of the present invention by adjusting the ATR conditions in a manner apparent to the skilled artisan in accordance with the teaching herein. Adiabatic treatment of the ATR inlet gas mixture in the ATR 12 to produce a synthesis gas comprises partially combusting the hydrocarbon feed gas of the ATR inlet gas mixture to exothermically oxidize a portion thereof and contacting the methane component of the hydrocarbon feed gas in the ATR inlet gas mixture with steam in the presence of a steam reforming catalyst, such as nickel-containing catalysts well known in the art, to endothermically reform the methane and steam. The ATR 12 is preferably maintained at a temperature in a range of about 900 to 1,050° C. and a pressure in a range of about 900 to 1,100 kPa.

An ATR outlet line 50 removes the synthesis gas from the ATR 12 at a rate of about 45,000 to 66,000 m$^3$/hr. The synthesis gas exiting the ATR 12 preferably has a molar composition of about 2.0 moles of hydrogen per mole of carbon monoxide, a temperature in a range of about 900 to 1,050° C., and a pressure in a range of about 800 to 950 kPa. The ATR outlet line 50 conveys the synthesis gas from the ATR 12 to an ATR condenser 52. Serially positioned in the ATR outlet line 50, however, upstream of the ATR condenser 52 are a plurality of heat exchangers including a steam conversion heat exchanger 54, a separator tail gas heat exchanger 56, the hydrocarbon feed gas heat exchanger 38, and an FIT reactor feed gas heat exchanger 58. The steam conversion heat exchanger 54 utilizes the high-temperature synthesis gas exiting the ATR 12 to heat process water for steam conversion, while quenching the synthesis gas to a temperature in a range of about 500 to 650° C. The separator tail gas heat exchanger 56 utilizes the high-temperature synthesis gas to heat a tail gas exiting a product separator described hereafter downstream of the F/T reactor 14. The hydrocarbon feed gas heat exchanger 38 utilizes the high-temperature synthesis gas to heat the hydrocarbon feed gas to the ATR 12 as described above. The F/T reactor feed gas heat exchanger 58 utilizes the high-temperature synthesis gas to heat the synthesis gas to the F/T reactor 14.

The ATR outlet line 50 feeds the synthesis gas into the ATR condenser 52 at a rate of about 37,000 to 54,500 kg/hr, a temperature in a range of about 250 to 350° C., and a pressure in a range of about 600 to 900 kPa. The ATR condenser 52 cools the synthesis gas, condensing the water contained therein. A condenser outlet line 60 conveys the resulting mixture of cooled synthesis gas and water from the ATR condenser 52 to a scrubber 62 where the water is separated from the synthesis gas. A scrubber water outlet line 64 withdraws the water from the bottom of the scrubber 62 for conversion to steam and return to the system 10. A scrubber gas outlet line 66 withdraws the cooled synthesis gas from the top of the scrubber 62 at a rate of about 42,000 to 63,000 m$^3$/hr, a temperature in a range of about 20 to 50° C., and a pressure in a range of about 500 to 700 kPa. The scrubber gas outlet line 66 conveys the cooled synthesis gas to the synthesis gas compressor 20 of the Brayton cycle 16.

The synthesis gas compressor 20 compresses the synthesis gas to a pressure in a range of about 2000 to 3000 kPa and a temperature in a range of about 150 to 250° C. The synthesis gas compressor 20 is driven by the shaft 28 connected to the second gas turbine 24 which is driven by means described hereafter. An F/T reactor inlet line 68 conveys the compressed synthesis gas from the synthesis gas compressor 20 to the F/T reactor 14 at a rate of about 35,000 to 52,000 kg/hr. The F/T reactor feed gas heat exchanger 58 described above preheats the compressed synthesis gas to within a temperature range of about 200 to 240° C. and a pressure range of about 2,000 to 2,800 kPa before the synthesis gas is fed to the F/T reactor 14. Fischer-Tropsch reactors are generally known in the art and the present F/T reactor 14 is selected by the skilled artisan in accordance with the teaching provided herein to satisfy the performance requirements of the present process. In accordance with such teaching the F/T reactor 14 can be one or more packed tubular reactors in series or alternatively the F/T reactor 14 can be a fluidized bed reactor. In any case, the F/T reactor 14 is preferably charged with a cobalt-containing catalyst and is maintained at nearly isothermal conditions by means such as externally cooling the F/T reactor 14 with boiling water or some other cooling medium to remove the exothermic heat of reaction. The temperature of the F/T reactor 14 is preferably in a range of about 200 to 235° C. and the pressure is in a range of about 1,600 to 2,800 kPa, thereby reacting the CO and $H_2$ of the synthesis gas to form water and heavy hydrocarbons therefrom.

An F/T reactor outlet line 69 withdraws the entire F/T reactor product, comprising a mixture of light and heavy hydrocarbons, as well as alcohols, $CO_2$, nitrogen and steam, from the F/T reactor 14 at a rate of about 35,000 to 52,000 kg/hr, a temperature in a range of about 200 to 240° C., and a pressure in a range of about 1,600 to 2,800 kPa. The molar conversion of carbon monoxide in the F/T reactor 14 to hydrocarbons (including methane and heavier hydrocarbons), alcohols and $CO_2$ is preferably in a range of about 75 to 90%. The F/T reactor outlet line 69 feeds the F/T reactor product to an F/T reactor cooler 70 where the F/T reactor product is cooled to a temperature in a range of about 60 to 100° C., depending on the amount of waxes formed, and a pressure in a range of about 1,500 to 2,800 kPa, thereby condensing the F/T reactor product to form a first product mixture comprising a liquid portion and a vapor portion. The liquid portion of the first product mixture contains heavy hydrocarbon liquids and water.

An F/T reactor cooler outlet line 71 conveys the first product mixture to a heavy product separator 72 where the vapor portion of the first product mixture is separated from the liquid portion. A heavy product separator vapor outlet line 73 conveys the separated vapor portion to an F/T reactor condenser 74 where it is further cooled to a temperature in a range of about 5 to 50° C., thereby forming a second product mixture comprising a liquid portion and a gas portion. The liquid portion of the second product mixture contains light hydrocarbon liquids and water. An F/T reactor condenser outlet line 75 conveys the second product mixture to a light product separator 76 where the gas portion of the second product mixture is separated from the liquid portion. A separator tail gas outlet line 77 withdraws the gas portion of the F/T reactor product as a separator tail gas from the top of the light product separator 76 at a rate of about 22,000 to 32,000 m$^3$/hr, a temperature in a range of about 5 to 50° C., and a pressure in a range of about 900 to 2,500 kPa. The separator tail gas serves as the LHV fuel gas for the present combustion process.

The separator tail gas outlet line 77 is provided with a tail gas pressure control valve 80 to adjust the pressure in the light product separator 76 within a range of about 1,500 to 2,800 kPa. The separator tail gas outlet line 77 splits into an excess tail gas line 82 and the LHV fuel gas feed line 444 at a junction point 78. The LHV fuel gas feed line 444 is provided with the separator tail gas heat exchanger 56 which functions in place of the steam-heated LHV fuel gas preheater 450 described in the embodiment of FIG. 3. The separator tail gas heat exchanger 56 elevates the temperature of the separator tail gas in the LHV fuel gas feed line 444 to a range of about 250 to 400° C. using the high-temperature synthesis gas from the ATR outlet line 50 as the heat transfer medium. The excess tail gas line 82 enables withdrawal of excess separator tail gas from the system 10 during process start-up or in response to process upsets. A flare (not shown) external to the system 10 is provided to dispose of the excess separator tail gas. The flare is accessed through a flare valve 84 in the excess tail gas line 82, preventing the pressure upstream in the LHV fuel gas feed line 444 from becoming too high.

The heavy product separator 72 further separates the liquid portion of the first product mixture into the heavy hydrocarbon liquids and water. The light product separator 76 similarly separates the liquid portion of the second product mixture into the light hydrocarbon liquids and water. A heavy hydrocarbon liquid outlet line 85 withdraws the heavy hydrocarbon liquids from the heavy product separator 72 and a light hydrocarbon liquid outlet line 86 withdraws the light hydrocarbon liquids from the light heavy product separator 76. The hydrocarbon liquid outlet lines 85, 86 join to form a common hydrocarbon liquid outlet line 87 mixing the heavy and light hydrocarbon liquids therein, resulting in the recovery of a synthetic hydrocarbon liquid as the desired product of the system 10 at a rate in a range of about 3.0 to 6.6 m$^3$/hr. The synthetic hydrocarbon liquid product preferably has a composition resembling that of a highly paraffinic crude condensate as, for example, represented by the following composition ranges: 0.5 to 10% LPG, 15 to 35% naphtha, 35 to 65% distillate, and 5 to 30% lube stock and waxes, depending on the catalyst and reactor conditions. The ratio of synthetic hydrocarbon liquid to water in the total liquids recovered from the F/T reactor product is in a range of about 0.45:1 to 1:1.

A first water outlet line 88 withdraws the water from the heavy product separator 72 and a second water outlet line 89 withdraws the water from the light product separator 76 at a combined rate of about 4.8 to 7.8 m$^3$/hr. The water outlet lines 88, 89 convey the water to a pump inlet manifold 90 where they combine with the scrubber water outlet line 64 to form a single water stream exiting the pump inlet manifold 90 via a pump inlet line 92. The pump inlet line 92 conveys the water to a multi-stage centrifugal pump 94 at a rate of about 6.5 to 10.5 m³/hr. The pump 94 elevates the pressure of the water therein to a pressure within a range of about 1,500 to 4,500 kPa and discharges the pressurized water to a pump outlet line 96. The steam conversion heat exchanger 54 is provided in the pump outlet line 96 to heat the pressurized water therein, using the high-temperature synthesis gas from the ATR outlet line 50 as the heat transfer medium. The steam conversion heat exchanger 54 elevates the temperature of the pressurized water to a range of about 300 to 570° C. and at a pressure range of about 1,400 to 4,500 kPa, thereby converting the water in the pump outlet line 96 to steam.

The pump outlet line 96 splits at a junction point 97 downstream of the steam conversion heat exchanger 54 into an ATR steam inlet line 98 and a combustor steam feed line 100. The ratio of steam fed to the ATR steam inlet line 98 and to the combustor steam feed line 100 is in a range of about 0.1:1 to 0.4:1. The ATR steam inlet line 98 extends to the ATR carburetor 44 and is provided with an ATR steam flow control valve 104 upstream thereof to adjust the steam flowrate within a range of about 1,100 to 2,700 kg/hr. The ATR carburetor 44 joins the ATR steam inlet line 98, the hydrocarbon feed gas inlet line 34 and an ATR air inlet line 106.

The combustor steam feed line 100 extends from the junction point 97 to the LHV fuel gas header 462 and is provided with a combustor steam pressure control valve 110 upstream of the LHV fuel gas header 462 to regulate the steam back-pressure within a range of 1,400 to 4,500 kPa. The combustor 30 operates in a substantially similar staged manner as described in the embodiment of FIG. 3, thereby producing the combustion products which are conveyed via the combustor outlet line 112 to the gas manifold 116. The combustion products typically have a molar composition in a range of about 69 to 75% $N_2$, 0.4 to 12% $O_2$, 3 to 7% $CO_2$, 10 to $H_2O$, and trace carbon monoxide and oxides of nitrogen. The combustion products are supplied to the gas manifold 116 at a rate of about 55,000 to 152,000 kg/hr, a temperature in a range of about 800 to 1,000° C., and a pressure in a range of about 900 to 1,100 kPa. The gas manifold 116 joins the combustor outlet line 112 to the first gas turbine 22. The cooling air line 118 conveys cooling air into the turbine blades and discs (not shown). Accordingly, the mixture of air and combustion products flows through the first gas turbine 22, functioning as a drive gas. The mixture is supplied to the first gas turbine at a rate in a range of about 55,500 to 156,000 kg/hr, a temperature in a range of about 750 to 1000° C. and a pressure in a range of about 900 to 1,100 kPa. The shaft 26 mechanically links the first gas turbine 22 to the air compressor 18, thereby driving the air compressor 18.

A first gas turbine outlet line 122 conveys the outlet gas from the first gas turbine 22 to the second gas turbine 24. The outlet gas is typically supplied to the second gas turbine 24 at a rate of about 56,000 to 156,000 kg/hr, a temperature in a range of about 600 to 850° C., and a pressure in a range of about 200 to 400 kPa. The outlet gas from the first gas turbine 22 becomes the drive gas for the second gas turbine 24. The shaft 28 mechanically links the second gas turbine 24 to the synthesis gas compressor 20, thereby driving the synthesis gas compressor 20. The shaft 28 may also be mechanically linked to an electrical generator (not shown) providing electric power for other on-site uses and/or for export. A second gas turbine outlet line 124 conveys the spent drive gas from the second gas turbine 24 to a flue 126 at a rate in a range of about 56,000 to 156,000 kg/hr, a temperature in a range of about 400 to 650° C. and a pressure near atmospheric. The flue 126 conveys the spent drive gas and exhausts it from the system 10. The flue gas exhausted from the flue 126 typically has a molar composition in a range of about 65 to 75% $N_2$, 0.5 to 12% $O_2$, 3 to 7% $CO_2$, 10 to 24% $H_2O$ and trace carbon monoxide and oxides of nitrogen.

The system 10 further comprises the air feed inlet line 128 through which an air feed is supplied directly to the air compressor 18. The air feed is typically fed through the air feed inlet line 128 at a rate in a range of about 55,000 to 152,000 kg/hr, a temperature of about 15° C. or ambient, and a pressure at about atmospheric. The air compressor 18 compresses the air feed to a pressure in a range of about 700 to 1,100 kPa and a temperature in a range of about 300 to 350° C. The air compressor outlet 130 conveys the compressed air feed to a junction point 132 at a rate in a range of about 55,000 to 152,000 kg/hr where the air compressor outlet 130 splits into the cooling air line 118 and an air takeoff line 134. The amount of air fed to the cooling air line 118 relative to the air takeoff line 134 is in a range of about 1 to 5%. The cooling air line 118 conveys its portion of the compressed air feed to the blades and discs of the first gas turbine 22 as described above. The air takeoff line 134 conveys the remainder of the compressed air feed to a first junction point 136 where the air takeoff line 134 splits into the ATR air inlet line 106, the combustion air inlet line 138, and the air bleed line 140. The ratio of air fed to the ATR air inlet line 106 and to the combustion air inlet line 138 is in a range of about 0.25:1 to 2.5:1. The air bleed line 140 normally has no flow therethrough except in the event of an excess pressure build-up in the air takeoff line 134 during start-up, upset conditions or at low feed rates of the hydrocarbon feed gas. The air bleed line 140 is provided with a back pressure control valve 142 connected to an air vent 144 should such an excess pressure build-up in the air take-off line 134 occur. The combustion air inlet line 138 extends from the first air junction point 136 to the combustor 30 and is provided with an air flow control valve 152 or fixed orifice (not shown) to adjust the air flow rate in the line 138 from about 13,000 to 43,000 kg/hr, thereby providing a sufficient air feed to maintain combustion within the combustor 30.

The combustion products exiting the combustor 30 to the gas manifold 116 are cooled to a temperature below the maximum temperature allowable in the first gas turbine 22, typically in a range of about 800 to 1000° C. depending on the metallurgy of the turbine 22. The combustor 30 may contain a catalyst to promote the combustion reactions therein, particularly when the molar conversion of CO in the F/T reactor 14 approaches 90%. Use of a catalyst may desirably minimize the size requirements of the air compressor 18 and maximize the amount of compressed air which may be withdrawn via the ATR air inlet line 106 and fed to the ATR 12.

The ATR air inlet line 106 extends from the junction point 136 to the ATR carburetor 44 described above and conveys its remaining portion of the compressed air feed to the ATR carburetor 44. The ATR air inlet line 106 is provided with an ATR air inlet flow control valve 158 to vent the air feed from the line 106, thereby adjusting the air flowrate in the line 106 within a range of about 30,500 to 52,500 kg/hr.

Figure 5:
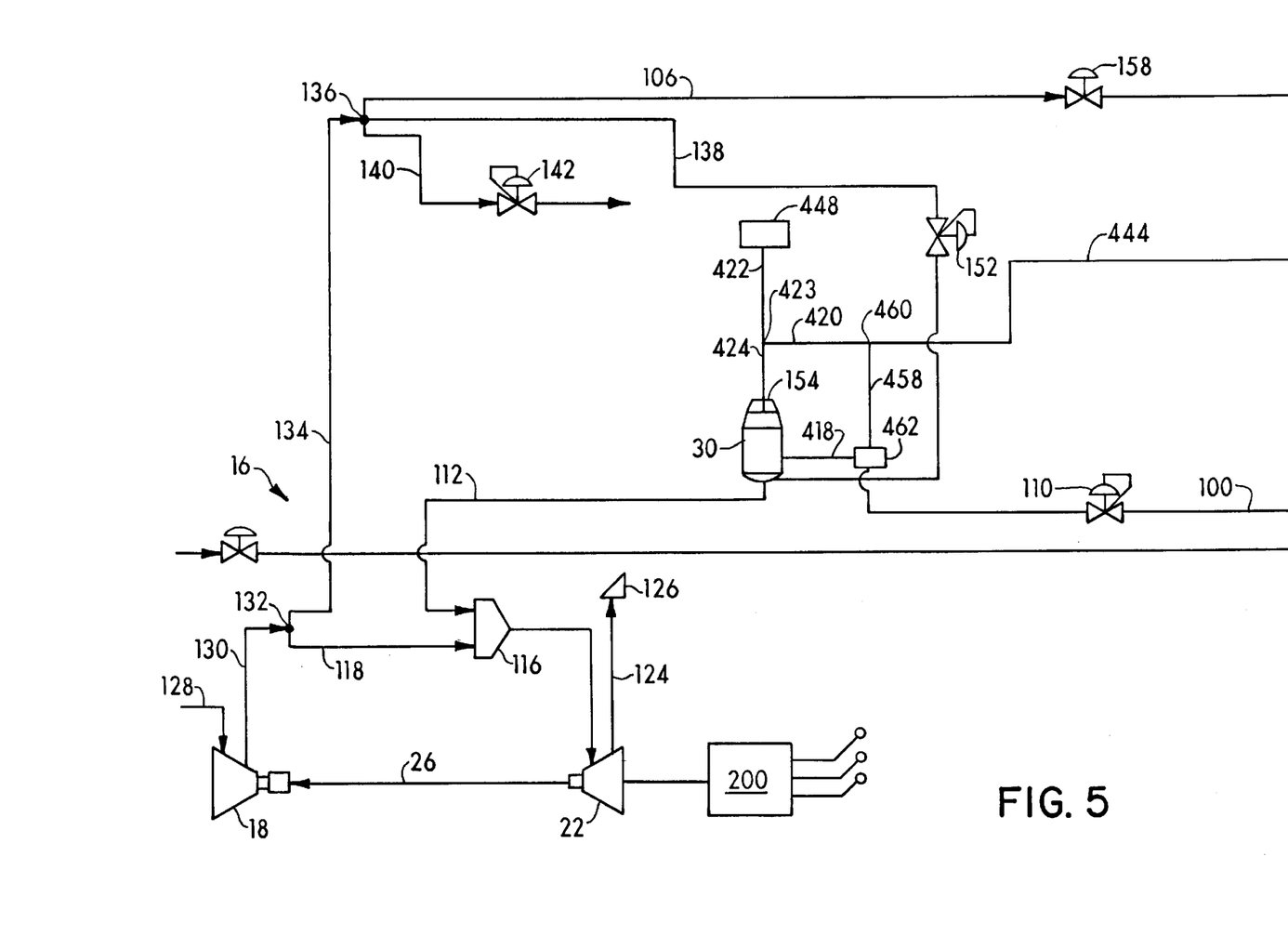
FIG. 5 is a schematic of another embodiment of the hydrocarbon conversion process shown in FIG. 4 having an alternate Brayton cycle.

Referring to FIG. 5, an alternate embodiment of the present invention is shown. The embodiment of FIG. 5 is essentially the same as the embodiment of FIG. 4 with the exception of modifications to the Brayton cycle. Accordingly, FIG. 5 shows essentially only the Brayton cycle of a hydrocarbon gas conversion system, the remainder of the system being substantially the same as the system 10 of FIG. 4. The Brayton cycle of FIG. 5 is generally designated 16'. The remaining components of the system shown in FIG. 5 which are common to both the embodiments of FIGS. 4 and 5 are designated by common reference characters. The Brayton cycle 16' comprises a single gas turbine 22' linked by a single shaft 26' to both an air compressor 18' and an electrical generator 200. The electrical generator 200 provides electric power to an electric motor (not shown) which drives the synthesis gas compressor and also provides electric power for export. As in the Brayton cycle 16 of FIG. 4, the combustor outlet line 112 conveys the combustion products from the combustor 30 to the gas manifold 116 which joins the combustor outlet line 112 to the gas turbine 22'. Although not shown, alternate Brayton cycle configurations are within the purview of the skilled artisan applying the foregoing teaching and such configurations are within the scope of the present invention.

While the foregoing preferred embodiments of the invention have been described and shown, it is understood that alternatives and modifications, such as those suggested and others, may be made thereto and fall within the scope of the present invention.

I claim:

1. A process for combusting a low heating value fuel gas to drive a gas turbine comprising:
   a) dividing a low heating value fuel gas feed into a burner portion and a combustion chamber portion;
   b) conveying said combustion chamber portion and a combustion air into a mixing zone to form an air/fuel mixture;
   c) conveying said burner portion into a flame zone through a burner nozzle while conveying a first portion of said air/fuel mixture into said flame zone through a burner port;
   d) contacting said burner portion and said first portion of said air/fuel mixture in said flame zone to combust said burner portion and said first portion and produce flame zone products;
   e) conveying said flame zone products into an oxidation zone downstream of said flame zone while conveying a second portion of said air/fuel mixture into said oxidation zone and combusting said second portion in said oxidation zone in the presence of said flame zone products to produce combustion products; and
   f) conveying said combustion products into a gas turbine and driving said gas turbine with said combustion products.

2. The process of claim 1 wherein the ratio of combustible components to air conveyed into said flame zone is a substantially stoichiometric ratio.

3. The process of claim 1 wherein the ratio of combustible components to air in said air/fuel mixture is a substoichiometric ratio.

4. The process of claim 1 wherein said flame zone and said oxidation zone are enclosed in a combustion liner positioned within a combustor casing to form an annulus between said liner and said casing, further wherein said mixing zone is positioned in said annulus upstream of said burner nozzle.

5. The process of claim 1 further comprising mixing a high heating value fuel gas feed with said burner portion of said low heating value fuel gas feed to form a burner fuel gas conveyed into said flame zone through said burner nozzle.

6. The process of claim 2 wherein said substantially stoichiometric ratio supports a diffusion combustion flame in said flame zone.

7. The process of claim 4 wherein said second portion of said air/fuel mixture is conveyed into said oxidation zone from said mixing zone through a combustion chamber port in said combustion liner.

8. The process of claim 7 wherein said combustion chamber portion of aid low heating value fuel gas feed is conveyed into said mixing zone through an injector in said combustor casing.

9. The process of claim 1 wherein said combustion chamber portion of aid low heating value fuel gas is larger than said burner portion.

10. The process of claim 1 wherein said combustion chamber portion and said combustion air are mixed in said mixing zone at a relatively high velocity and said burner portion and said first portion of said air/fuel mixture are contacted in said flame zone at a relatively low velocity.

11. A combustor for combusting a low heating value fuel gas comprising:
   a) first dividing means for dividing a low heating value fuel gas feed into a burner portion and a combustion chamber portion;
   b) means for mixing said combustion chamber portion and a combustion air to form an air/fuel mixture;
   c) second dividing means for dividing said air/fuel mixture into a first portion and a second portion;
   d) a burner nozzle in fluid communication with said first dividing means having a burner nozzle outlet and a burner nozzle inlet for receiving said burner portion;
   e) a burner port in fluid communication with said second dividing means and having a burner port outlet and a burner port inlet for receiving said first portion of said air/fuel mixture;
   f) a flame zone in fluid communication with and downstream of said burner nozzle outlet and said burner port outlet for receiving and combusting said burner portion and said first portion of said air/fuel mixture to produce flame zone products; and
   g) an oxidation zone in fluid communication with and downstream of said flame zone for receiving said flame zone products and said second portion of said air/fuel mixture and for combusting said second portion of said air/fuel mixture in the presence of said flame zone products to produce combustion products.

12. The combustor of claim 11 further comprising means for mixing a high heating value fuel gas feed with said burner portion of said low heating value fuel gas feed upstream of said burner nozzle.

13. A process for converting a lighter hydrocarbon gas to heavier hydrocarbons comprising:
   a) reacting a first portion of an air feed and a lighter hydrocarbon feed gas to produce a synthesis gas comprising hydrogen and carbon monoxide;
   b) reacting said synthesis gas in the presence of a hydrocarbon synthesis catalyst to produce heavier hydrocarbons, a tail gas and water;
   c) dividing said tail gas into a burner portion and a combustion chamber portion;
   d) conveying said combustion chamber portion and a second portion of said air feed into a mixing zone to form an air/fuel mixture;
   e) conveying said burner portion into a flame zone through a burner nozzle while conveying a first portion of said air/fuel mixture into said flame zone through a burner port;

f) contacting said burner portion and said first portion of said air/fuel mixture in said flame zone to combust said burner portion and said first portion and produce flame zone products;

g) conveying said flame zone products into an oxidation zone downstream of said flame zone while conveying said second portion of said air/fuel mixture into said oxidation zone and combusting said second portion in said oxidation zone in the presence of said flame zone products to produce combustion products;

h) generating mechanical power with said combustion products; and i) compressing said air feed with said mechanical power.

14. The process of claim 13 wherein said tail gas contains at least about 80 mole percent inert non-combustible components.

15. The process of claim 13 wherein the ratio of combustible components to air conveyed into said flame zone is a substantially stoichiometric ratio.

16. The process of claim 13 wherein the ratio of combustible components to air in said air/fuel mixture is a substantially substoichiometric ratio.

17. The process of claim 13 further comprising mixing a high heating value fuel gas feed with said burner portion of said low heating value fuel gas feed to form a burner fuel gas conveyed into said flame zone through said burner nozzle.

18. The process of claim 15 wherein said substantially stoichiometric ratio supports a diffusion combustion flame in said flame zone.

19. The process of claim 13 wherein said combustion chamber portion of said low heating value fuel gas is larger than said burner portion.

20. The process of claim 13 wherein said combustion chamber portion and said combustion air are mixed in said mixing zone at a relatively high velocity and said burner portion and said first portion of said air/fuel mixture are contacted in said flame zone at a relatively low velocity.

21. The process of claim 13 wherein said flame zone and said oxidation zone are enclosed in a combustion liner positioned within a combustor casing to form an annulus between said liner and said casing, further wherein said mixing zone is positioned in said annulus upstream of said burner nozzle.

22. The process of claim 21 wherein said second portion of said air/fuel mixture is conveyed into said oxidation zone from said mixing zone through a combustion chamber port in said combustion liner.

23. The process of claim 21 wherein said combustion chamber portion of said low heating value fuel gas feed is conveyed into said mixing zone through an injector in said combustor casing.

* * * * *